(12) United States Patent
Koarashi

(10) Patent No.: US 12,029,867 B2
(45) Date of Patent: Jul. 9, 2024

(54) INSERTING MEMBER FIXING DEVICE

(71) Applicant: HI-LEX CORPORATION, Takarazuka (JP)

(72) Inventor: Shinsaku Koarashi, Takarazuka (JP)

(73) Assignee: HI-LEX CORPORATION (JP)

( * ) Notice: Subject to any disclaimer, the term of this patent is extended or adjusted under 35 U.S.C. 154(b) by 706 days.

(21) Appl. No.: 17/290,801

(22) PCT Filed: Nov. 28, 2019

(86) PCT No.: PCT/JP2019/046574
§ 371 (c)(1),
(2) Date: May 3, 2021

(87) PCT Pub. No.: WO2020/111183
PCT Pub. Date: Jun. 4, 2020

(65) Prior Publication Data
US 2021/0402150 A1 Dec. 30, 2021

(30) Foreign Application Priority Data
Nov. 28, 2018 (JP) .................. 2018-222563

(51) Int. Cl.
*A61M 25/01* (2006.01)
*A61M 25/02* (2006.01)
(Continued)

(52) U.S. Cl.
CPC ........ *A61M 25/02* (2013.01); *A61M 39/0613* (2013.01); *A61M 60/178* (2021.01);
(Continued)

(58) Field of Classification Search
CPC .. A61M 25/02; A61M 39/0613; A61M 39/02; A61B 90/10; A61B 90/14
See application file for complete search history.

(56) References Cited

U.S. PATENT DOCUMENTS

2007/0083157 A1 4/2007 Belley et al.
2013/0046241 A1 2/2013 Okamura et al.
(Continued)

FOREIGN PATENT DOCUMENTS

CN 102811760 A 12/2012
CN 106415032 A 2/2017
(Continued)

OTHER PUBLICATIONS

The State Intellectual Property Office (SIPO) of People's Republic of China (PRC), "Notification to Grant Patent Right for Invention" dated Jun. 22, 2022 for application No. CN 201980075779.4 listing seven cited patent documents, 5 pages.
(Continued)

*Primary Examiner* — Nathan R Price
*Assistant Examiner* — Tania Ismail
(74) *Attorney, Agent, or Firm* — Ware, Fressola, Maguire & Barber LLP

(57) ABSTRACT

This device is an inserting member fixing device to fix a linear inserting member to an insertion target, the inserting member fixing device comprising: a main body; a chuck portion; an inner sealing portion to be brought into close contact with an outer periphery of the inserting member; an inserting member supporting portion to support the inserting member; and a movement restricting portion to restrict movement of the inner sealing portion and the inserting member supporting portion. The inserting member supporting portion and the inner sealing portion are provided adjacent to each other in an axial direction of the inserting member, and a space is provided between the inserting member supporting portion and the inner sealing portion so that a main body-side end portion of the inserting member supporting portion is displaceable when the inserting member swings.

4 Claims, 3 Drawing Sheets

(51) Int. Cl.
*A61M 39/06* (2006.01)
*A61M 60/178* (2021.01)
*A61M 60/88* (2021.01)
*A61B 90/10* (2016.01)
*A61B 90/14* (2016.01)
*A61M 39/02* (2006.01)

(52) U.S. Cl.
CPC .............. *A61M 60/88* (2021.01); *A61B 90/10* (2016.02); *A61B 90/14* (2016.02); *A61M 39/02* (2013.01)

(56) References Cited

U.S. PATENT DOCUMENTS

| | | |
|---|---|---|
| 2015/0102245 A1 | 4/2015 | Chen |
| 2017/0198744 A1 | 7/2017 | Sano |
| 2019/0290887 A1 | 9/2019 | Ayuzawa |

FOREIGN PATENT DOCUMENTS

| | | |
|---|---|---|
| CN | 106691554 A | 5/2017 |
| CN | 204134042 U | 5/2021 |
| JP | H03-254758 A | 11/1991 |
| JP | 2017-104437 A | 6/2017 |
| JP | 2017104437 A * | 6/2017 |
| JP | 2019-166310 A | 10/2019 |
| KR | 101525126 B1 | 6/2015 |
| WO | 9325264 A1 | 12/1993 |

OTHER PUBLICATIONS

Partial (machine) translation of SIPO Notice of Grant Decision dated Jun. 22, 2022 for application No. CN 201980075779.4, 2 pages.

English translation of the International Search Report, International Application No. PCT/JP2019/046574, mailed Feb. 10, 2020, 3 pages.

* cited by examiner

INSERTING MEMBER FIXING DEVICE

TECHNICAL FIELD

The invention relates to an inserting member fixing device to fix an inserting member to an insertion target.

BACKGROUND ART

Conventionally, as a device to fix, to an insertion target, an inserting member to be inserted through the insertion target, a holding mechanism assembly shown in Patent document 1 is known, for example.

The holding mechanism assembly disclosed in Patent document 1 comprises a driveline being an inserting member, a fixing member having an insertion portion, to which the driveline is inserted, to be fixed to the skin being an insertion target of the driveline, and a holding structure to hold the driveline to the fixing member. The holding structure comprises a chuck member and a sealing member to be arranged on the outer periphery of the inserting member in the insertion portion, and a screw member to be inserted and screwed into an opening on the outer side of the insertion portion. In the insertion portion, by screwing the screw member into the insertion portion with the fixing member-side abutment portion of the chuck member abutting the insertion portion inclined surface of the insertion portion, a tip abutment portion of the screw member presses the chuck member and the chuck member-side contact surface of the sealing member presses the chuck member. In this way, the driveline is held in close contact to the fixing member. Moreover, a configuration is disclosed in which a tubular-shaped kink guard is provided at an end on the outside of the body of the screw member of the above-configured holding mechanism assembly, preventing bending of and torsion in the radial direction of the driveline being led out from the holding mechanism assembly. In the kink guard, a fitting portion to be fitted to a fitting hole of the screw portion is positioned adjacent to the sealing member.

PRIOR ART DOCUMENT

Patent Document

Patent Document 1: JP 2017-104437 A

SUMMARY OF THE INVENTION

Problem to be Solved by the Invention

However, with the conventional holding structure, in a case of a large swing of a driveline due to an external force applied to the driveline, a load applied to the kink guard in the radial direction of the kink guard is transmitted to a fitting portion being a portion to be fitted to a screw member, possibly causing a sealing member abutting the fitting portion to be deformed. As a result, the sealing function of the sealing member, in particular, the close contactability between the sealing member and the driveline could be reduced.

An object of the invention is to provide an inserting member fixing device in which suppressing of swinging of an inserting member such as a driveline and securing of sealing can be made compatible.

Means to Solve the Problem

An inserting member fixing device according to the invention is an inserting member fixing device to fix a linear inserting member to an insertion target, the inserting member fixing device comprising:

a main body;
a chuck portion to grasp the inserting member;
an inner sealing portion to be brought into close contact with an outer periphery of the inserting member;
an inserting member supporting portion to support the inserting member to maintain the inserting member being in a line shape; and
a movement restricting portion to restrict movement of the inner sealing portion and the inserting member supporting portion, wherein the main body has a first opening, a second opening, and a communicating portion to communicate the first opening and the second opening, and a fixing portion to be fixed to the insertion target, the chuck portion has an insertion portion to which the inserting member is inserted, and a contact portion being provided on an outer periphery of the chuck portion to contact an inner wall of the communicating portion of the main body;

the inner sealing portion has a through-hole to which the inserting member is inserted to allow an inner periphery of the through-hole to be in close contact onto the outer peripheral surface of the inserting member, the movement restricting portion has a main body connecting portion to be connected to the main body at the first opening side of the main body, an inner sealing portion pressing portion to press an outer periphery of the inner sealing portion inwardly, and an abutment portion to abut an outer periphery of the inserting member supporting portion, the inserting member supporting portion has end portions provided at both ends in a length direction, a supporting portion to abut the outer periphery of the inserting member to support the inserting member, and a sandwiched portion sandwiched and held by the abutment portion of the movement restricting portion and the inserting member, the inserting member supporting portion and the inner sealing portion are provided adjacent to each other in an axial direction of the inserting member, and a space is provided between the inserting member supporting portion and the inner sealing portion so that a main body-side end portion of the inserting member supporting portion is displaceable when the inserting member swings.

Effects of the Invention

According to the invention, suppressing of swinging of an inserting member such as a driveline and securing of a sealing can be made compatible.

EMBODIMENT FOR CARRYING OUT THE INVENTION

Below, an embodiment of the invention is explained in detail with reference to the drawings.

<Relationship Between Inserting Member Fixing Device 1 and Inserting Member 2>

Figure 1:
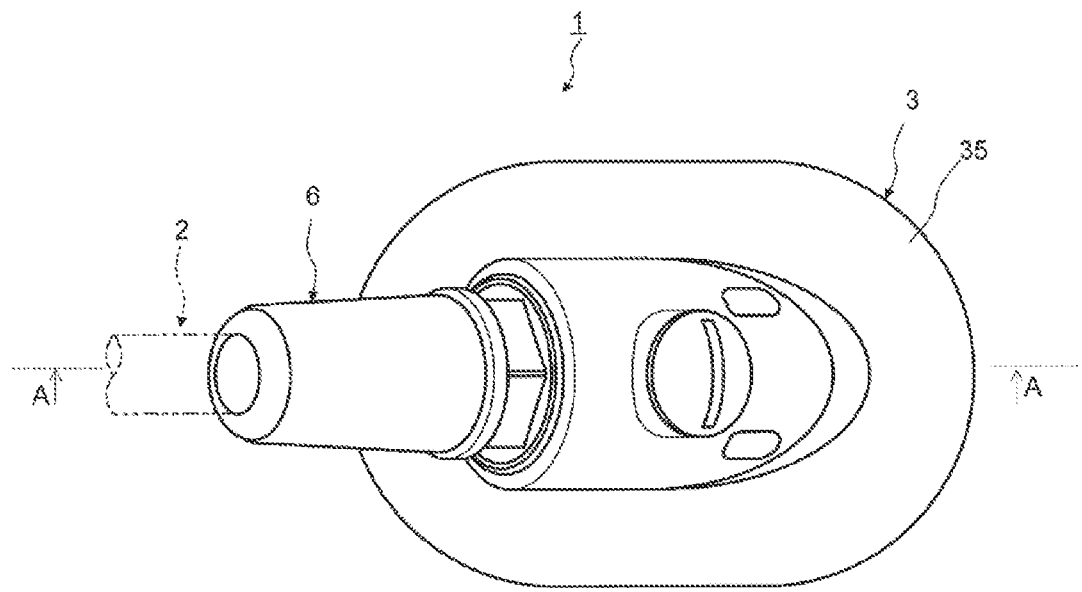
FIG. 1 shows a plan view of an appearance of an inserting member fixing device according to an embodiment of the invention.
Figure 2:
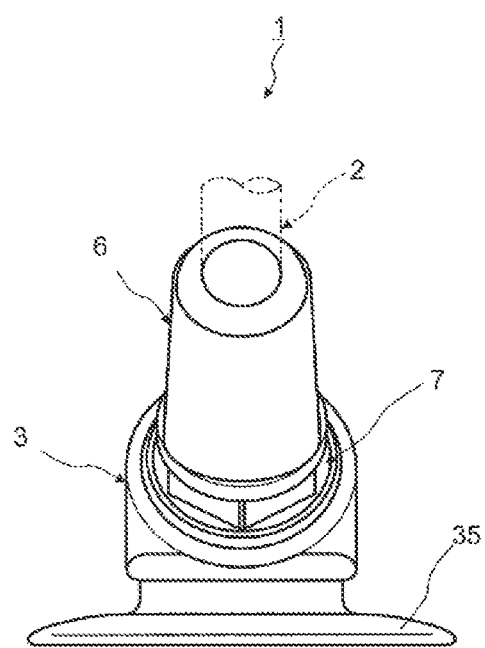
FIG. 2 shows a rear view of an appearance of the inserting member fixing device according to the embodiment of the invention.
Figure 3:
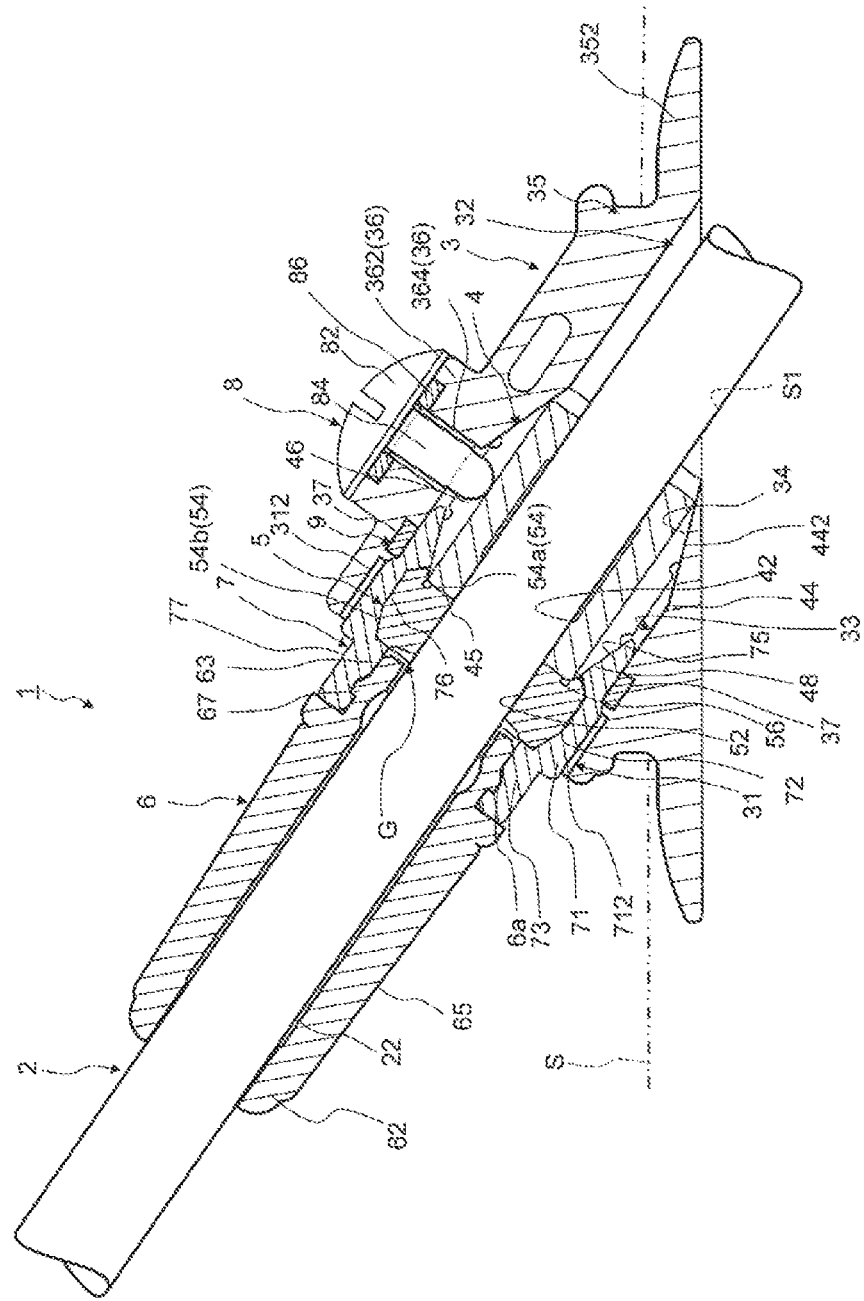
FIG. 3 shows a cross-sectional view as viewed from an arrow A-A in FIG. 1.
Figure 4:
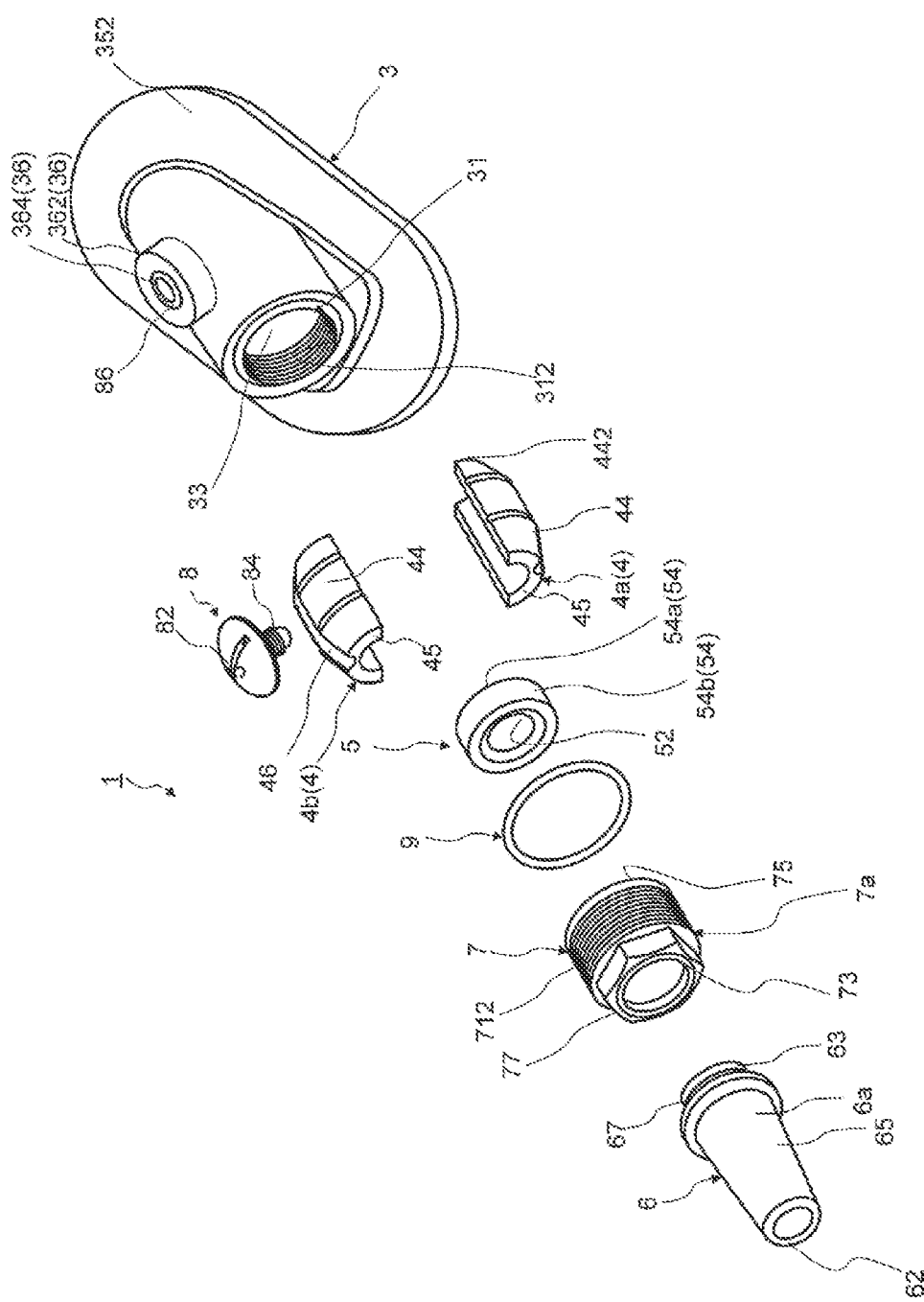
FIG. 4 shows an exploded perspective view of the inserting member fixing device according to the embodiment of the invention.

An inserting member fixing device 1 in the embodiment fixes a linear inserting member 2 to an insertion target of the inserting member 2. The inserting member fixing device 1 holds and fixes the inserting member 2 with the inserting member 2 being inserted through the inserting member fixing device 1 so as to be present at least across the interior and the exterior of the inserting member fixing device 1 when fixing the inserting member 2. The inserting member 2 may pass through the insertion target or may not pass through the insertion target as long as a portion of the inserting member 2 being inserted through the insertion target is held by the inserting member fixing device 1. In the embodiment, the insertion target is a skin S having a hole S1 (see FIG. 3) for inserting the inserting member 2 through the hole S1, and the inserting member 2 is inserted through the hole S1.

The inserting member 2 is a linear member having a predetermined length, and, in the embodiment, the inserting member 2 is a driveline which is a type of medical tube. The driveline is a wiring needed to drive and control a ventricular assist device (VAD) arranged in a body cavity. The ventricular assist device has a pump to circulate blood in the body. A device arranged outside the body has a pressure-feeding pump to send out cooling water to cool a pump of the ventricular assist device, and a power source to feed electric power to the pump of the ventricular assist device. The driveline is a tubular-shaped member to be inserted into inside of the human body. The outer surface of the driveline is covered with fiber. In the embodiment, an end of the driveline inside the body is connected to a medical device (not shown; for example, the VAD) being arranged inside the body, while an end of the driveline outside the body is connected to a device (not shown) being arranged outside the body.

In the embodiment, in the interior of the driveline, a cooling water circulation path to circulate cooling water between the pressure-feeding pump and the ventricular assist device and a power cable to connect the power source and the pump are wired. The configuration of the driveline is not limited thereto. For example, the driveline may have only the power cable, or the driveline may have only the cooling water circulation path, or the driveline may have a member having a different function.

The driveline is inserted into inside the body from the skin S (see FIG. 3) being the insertion site of a subject to be examined and is guided such that the driveline reaches an object site (the VAD in the embodiment). In a case of fixing the driveline, an infection control measure for a bacterial infection, or a so-called driveline infection measure, in the skin S being the insertion site, is necessary.

The inserting member fixing device 1 in the embodiment can suppress swinging of the inserting member 2 (driveline) to be inserted through the skin S being the insertion target and secure the watertightness with the inserting member 2. In particular, the inserting member fixing device 1 can prevent the bacteria from passing along the outer periphery of the inserting member 2 through the hole S1 of the skin S to invade into the body even when the inserting member 2 swings. Thus, regardless of swinging of the inserting member 2, a portion between the inserting member fixing device 1 and the inserting member 2 is surely sealed to prevent development of a bacterial infection in the insertion site.

The inserting member 2 is not limited to the driveline. The inserting member 2 may be anything as along as the inserting member 2 is a linear one to be fixed to the insertion target with the inserting member 2 being inserted through the insertion target. For example, the inserting member 2 may be a catheter, a different medical tube, or a solid medical cable, or may be a linear member other than a medical cable. Moreover, while the insertion target to which the inserting member 2 is inserted is the skin S in the embodiment, the insertion target is not limited thereto. The insertion target may be a target having the need to suppress invasion of bacteria into an element making up an organism, such as the organ or bone.

<Configuration of Inserting Member Fixing Device 1>

Next, the inserting member fixing device 1 in the embodiment will be explained.

The inserting member fixing device 1 in the embodiment fixes the linear inserting member 2 to the insertion target. Fixing to the insertion target, in the embodiment, means fixing a main body 3 to the skin S by using a part of a fixing portion 35 of the main body 3 as an anchor for a part of the skin S (the insertion site).

In the embodiment, the inserting member fixing device 1 comprises the main body 3, a chuck portion 4, an inner sealing portion 5, an inserting member supporting portion 6, a movement restricting portion 7, and an outer sealing portion 9.

The main body 3 is fixed to the insertion target and the inserting member 2 is inserted into the main body 3. The main body 3 is attached so as to cover the hole S1 of the insertion target. The inserting member 2 to be inserted through the hole S1 is fixed to the main body 3 with the inserting member 2 being inserted through the main body 3.

The main body 3 has a first opening 31, a second opening 32, and a communicating portion 33 to communicate the first opening 31 and the second opening 32, a fixing portion 35 to be fixed to the insertion target, and a rotation preventing member mounting portion 36. The main body 3 preferably has the rigidity capable of fixing the main body 3 to the insertion target, and, in a case that the main body 3 has the fixing portion 35 to be fixed to the skin S being the biological tissues as in the embodiment, the main body 3 is preferably formed of a metal having a high biocompatibility. The metal having the high biocompatibility is titanium or a titanium alloy, for example. The fixing portion 35 has a surface formed of a porous material allowing invasion into cells, such as a meshed-shaped titanium fiber, to improve the close contactability between the fixing portion 35 and the skin S, achieving prevention of invasion of bacteria into the living body.

The inserting member 2 is inserted through the first opening 31, the second opening 32, and the communicating portion 33.

The first opening 31 is an opening being continuously provided on a side of outside the body of the communicating portion 33, while the second opening 32 is an opening being continuously provided on a side of inside the body.

The first opening 31 is formed such that the opening surface thereof is orthogonal with respect to an axial direction of the communicating portion 33. The second opening 32 is formed such that the opening surface thereof is non-orthogonal with respect to the axial direction of the communicating portion 33. The cross section of the first opening 31 is formed in a circular shape, the diameter of the cross section of the first opening 31, in the embodiment, is formed to have substantially the same length as the outer diameter of the movement restricting portion 7 to be screwed into the first opening 31.

A screwed portion 312 screwed with a main body connecting portion 71 of the movement restricting portion 7 is provided at an opening side of the first opening 31, and the movement restricting portion 7 is screwed into the first opening 31. In the embodiment, the screwed portion 312 is a female screw portion screwed with the main body connecting portion 71 being a male screw portion. Details of the main body connecting portion 71 will be described below.

The cross section of the second opening 32 is formed in an elliptical shape to which the inserting member 2 may be inserted in the second opening 32 while the inserting member 2 is inclined. The cross-sectional area of the second opening 32 is greater than the cross-sectional area of the inserting member 2 when the inserting member 2 is cut in a direction being parallel to the second opening 32.

The communicating portion 33 communicates the first opening 31 and the second opening 32 and the cross section of the communicating portion 33 is formed in a circular shape. In the embodiment, the communicating portion 33 is provided such that the central axis of the communicating portion 33 forms one straight line aligning with the axis of the first opening 31 and the axis of the second opening 32.

The communicating portion 33 is configured in a circular tube shape and houses the chuck member 4 in the interior of the communicating portion 33. In the embodiment, the communicating portion 33 is formed in a cylindrical shape such that the central region of the communicating portion 33 in the axial direction is expanded outwardly in the radial direction.

The communicating portion 33 has, at an inner surface of the communicating portion 33, an inclined inner peripheral surface 34 provided on the second opening 32 side such that the inner diameter of the inclined inner peripheral surface 34 is reduced toward the second opening 32 from the first opening 31.

When the chuck portion 4 is pressed from the first opening 31 side and moves toward the second opening 32, the outer surface of the chuck portion 4 on the second opening 32 side abuts the inclined inner peripheral surface 34, reducing the chuck portion 4 in diameter to cause the chuck member 4 to chuck the inserting member 2.

While the inclined inner peripheral surface 34 is provided such that the inclined angle thereof is constant in the embodiment, the inclined inner peripheral surface 34 is not limited thereto. For example, the inclined inner peripheral surface 34 may be formed in a cross-sectionally curved shape such that the inclined angle of the inclined inner peripheral surface 34 increases toward the second opening 32.

At the inner peripheral surface of the communicating portion 33, a concave portion 37 extending in the peripheral direction is provided on the first opening 31 side. In the above-mentioned concave portion 37, the outer sealing portion 9 which watertightly blocks the gap between the movement restricting portion 7 and the main body 3 is arranged.

The fixing portion 35 is a portion to be fixed to the skin S being the insertion target, and fixes the inserting member fixing device 1 to the insertion target. In detail, the fixing portion 35 is fixed to the skin S around the hole S1 provided in the skin S. In the embodiment, the fixing portion 35 has a flange portion 352 protruding in a non-parallel manner with respect to the direction in which the communicating portion 33 extends from the outer peripheral surface of the insertion site. Burying the above-mentioned flange portion 352, as an anchor, on the inner side of the skin S around the hole S1 allows the fixing portion 35 to be fixed to the skin S. In the embodiment, the direction in which the communicating portion 33 extends is inclined with respect to the flange portion 352.

The fixing portion 35 is configured to be integral with the communicating portion 33 so as to surround the communicating portion 33. While the fixing portion 35 is configured to be integral with the communicating portion 33, it is not limited thereto. For example, the fixing portion 35 formed in a flange shape as a separate body may be configured to be fixed, by soldering or adhering, onto the outer periphery on the second opening 32 side of a tubular-shaped body configuring the communicating portion 33.

The surface of the flange portion 352 may be provided with surface treatment such that the close contactability to a target to be fixed improves.

A rotation preventing member 8 engages a rotation-prevented portion 46 of the chuck portion 4 to be arranged in the communicating portion 33 and suppresses rotating of the chuck portion 4 around the axis of the chuck portion 4. In the embodiment, the rotation preventing member 8 is a screw having a head 82 and a shaft 84.

The rotation preventing member 8 is attached to a rotation preventing member mounting portion 36.

The rotation preventing member mounting portion 36 has a base portion 362 provided so as to protrude from the outer surface, and a through-hole 364. The through-hole 364 is formed in the base portion 362 and passes through the main body 3 between the communicating portion 33 of the main body 3 and the exterior of the main body 3. The rotation preventing member 8 is inserted into the through-hole 364. The protruding end of the base portion 362 forms a plane surface, and, when the shaft 84 of the rotation preventing member 8 is inserted into the through-hole 364, the head 82 of the rotation preventing member 8 is engaged with the protruding end of the base portion 362. In the embodiment, the shaft 84 is a male screw portion, and a female screw portion which is screwed with the shaft 84 is provided on the inner periphery of the through-hole 364. This allows the protruded length of the shaft 84 into the communicating portion 33 to be freely adjusted. A sealing portion 86 is arranged between the head 82 of the rotation preventing member 8 and the protruding end of the rotation preventing member mounting portion 36, watertightly blocking the gap therebetween.

The shaft 84 of the rotation preventing member 8 is inserted into the rotation-prevented portion 46 of the chuck portion 4. In this way, rotating of the chuck portion 4 around the axis thereof is suppressed.

The chuck portion 4 tightens and grasps the inserting member 2 and is fixed to the main body 3. In the embodiment, the chuck portion 4 is arranged between the inner peripheral surface of the communicating portion 33 and an outer periphery 22 of the inserting member 2 to be inserted through the communicating portion 33 and watertightly blocks the gap between the communicating portion 33 and the inserting member 2. The chuck portion 4 may be configured with any material as long as the chuck portion 4 may hold the inserting member 2 and watertightly block the gap between the communicating portion 33 and the inserting member 2. For the chuck portion 4, a material capable of being infinitesimally deformed such as to make it possible to tighten the inserting member 2 may be used. For example, the chuck portion 4 may be formed of, for example, a metal having a high corrosion resistance, such as titanium or a titanium alloy, and having the hardness equivalent to that of a metal forming the main body 3 or having the hardness lower than that of the metal forming the main body 3.

The chuck portion 4 is preferably configured to be a tubular-shaped body to tighten and grasp the inserting member 2. The chuck portion 4 may be configured to be a tubular-shaped body by integrally joining divided bodies being divided in the radial direction. The chuck portion 4 in the embodiment is configured by combining half-divided divided bodies 4a, 4b divided along a plane including the axis of the tubular-shaped body into two divisions in the radial direction. Moreover, the chuck portion 4 is not limited to having the structure capable of being divided in the radial direction, so that the chuck portion 4 may be configured to have the structure capable of being divided in the axial direction or the structure not capable of being divided into the divided bodies.

The chuck portion 4 has an insertion portion 42 to which the inserting member 2 is inserted, a contact portion 44 provided on the outer periphery of the chuck portion 4 to contact the inner peripheral surface of the communicating portion 33 of the main body 3, and a rotation-prevented portion 46.

The insertion portion 42 is arranged so as to surround the inserting member 2 and is formed to be capable of being reduced in diameter. The insertion portion 42 is reduced in diameter to be fitted on the outer periphery 22 of the inserting member 2 in close contact therewith.

In the embodiment, the insertion portion 42 is the entire inner peripheral surface of the chuck portion 4. The shape of the insertion portion 42 in a cross section is circular and the insertion portion 42 is formed such that the diameter of the insertion portion 42 in the cross section is uniform. While the insertion portion 42 is formed such that the diameter of the insertion portion 42 in the cross section is uniform, it is not limited thereto. For example, in the central portion of the insertion portion 42, the insertion portion 42 may have a stepped portion being formed such that the diameter of the insertion portion 42 in the cross section increases. In the embodiment, the inner periphery of the divided body 4a, 4b is configured to be a little smaller than the outer diameter of the inserting member 2, and the cross-sectionally half circle-shaped inner peripheral portions of the divided bodies 4a, 4b sandwiches the outer periphery 22 of the inserting member 2. In this case, when the divided bodies 4a, 4b moves inward in the radial direction, the divided bodies 4a, 4b can press and sandwich the inserting member 2 to hold the inserting member 2 in close contact with the outer periphery of the inserting member 2.

The contact portion 44 contacts the inner peripheral surface of the communicating portion 33 to cause the chuck portion 4 to closely contact, in a watertightly manner, with the communicating portion 33.

In the embodiment, the contact portion 44 is an outer peripheral surface of the chuck portion 4, in particular, has a contact surface 442 provided on the outer peripheral surface on the second opening portion 32 side to abut the inclined inner peripheral surface 34.

At the contact surface 442, the chuck portion 4 contacts the main body 3 by pressing of the movement restricting portion 7 toward the second opening 32 so that the chuck portion 4 moves inwardly in the radial direction of the inserting member 2 by a reaction force received from the main body 3 being in contact with the chuck portion 4.

In the embodiment, the contact surface 442 is configured by an inclined surface whose inclined angle is identical to that of the inclined inner peripheral surface 34. In other words, the contact surface 442 is configured to abut the inclined inner peripheral surface 34 in a surface contact with the inclined inner peripheral surface 34. In other words, it is preferable that the contact surface 442 has a portion whose inclined angle is identical to that of the inclined inner peripheral surface 34 on at least a portion of the contact surface 442.

The chuck portion 4 has, at an end portion on the first opening 31 side, a sealing abutment portion 45 to which the inner sealing portion 5 abuts and a restricting portion abutment portion 48 to which the movement restricting portion 7 abuts.

The sealing abutment portion 45 is configured with a part of an inclined surface at an end portion of the chuck portion 4, which inclined surface is formed on the first opening 31 side thereof, and a surface being parallel to the radial direction of the communicating portion 33 and is formed continuously with the restricting portion abutment portion 48. While the sealing abutment portion 45 is configured with the part of the inclined surface of the chuck portion 4, which inclined surface is formed on the first opening 31 side thereof, and the surface being parallel to the radial direction of the communicating portion 33, it is not limited thereto. It suffices that the sealing abutment portion 45 has a shape capable of receiving a force in a direction to push the chuck portion 4 toward the second opening portion 32 from the sealing abutment portion 45.

The restricting portion abutment portion 48 is a portion provided at an end on the first opening 31 side, with the chuck portion 4 being arranged in the communicating portion 33, to abut the movement restricting portion 7.

The restricting portion abutment portion 48 is configured to abut a chuck pressing portion 75 of the movement restricting portion 7 to apply a force to the chuck pressing portion 75 in a direction in which the chuck portion 4 is reduced in diameter. Details of the chuck pressing portion 75 will be described below.

Moreover, the chuck pressing portion 75 of the movement restricting portion 7 also receives, from the restricting portion abutment portion 48, a force outwardly in the radial direction of the movement restricting portion 7.

In the embodiment, the restricting portion abutment portion 48 is configured with an inclined surface whose inclined angle is identical to that of the chuck pressing portion 75 being an inclined surface. In other words, the restricting portion abutment portion 48 abuts the chuck pressing portion 75 in a surface contact with the chuck pressing portion 75. In other words, it is preferable that the restricting portion abutment portion 48 has an inclined surface whose inclined angle is identical to that of the inclined surface of the sealing abutment portion 45 in at least a portion of the restricting portion abutment portion 48.

While the restricting portion abutment portion 48 is configured with an inclined surface, it is not limited thereto. It suffices that the restricting portion abutment portion 48 at least has a shape capable of receiving a force in a direction to push the chuck portion 4 toward the second opening 32 from the movement restricting portion 7. Moreover, the chuck portion 4 may have a concave portion(s) in the peripheral direction on the outer peripheral surface of the chuck portion 4 to stop sliding when it is attached to the insertion target.

The rotation-prevented portion 46 engages with the rotation preventing member 8 attached to the main body 3 to restrict rotation of the chuck portion 4 around the axis of the chuck portion 4 in the communicating portion 33.

In the embodiment, the rotation-prevented portion 46 is provided on the outer peripheral surface of the chuck portion 4. The rotation-prevented portion 46 is formed in a groove shape extending in the axial direction.

In the embodiment, the rotation-prevented portion 46 is provided in each of the divided bodies 4a, 4b, and, when the divided bodies 4a, 4b are provided in the communicating portion 33 to form the chuck portion 4, the rotation-prevented portion 46 can be easily arranged at a position corresponding to the rotation preventing member 8. In the embodiment, the shaft 84, which protrudes into the communicating portion 33 from the base portion 362 of the rotation preventing member mounting portion 36 of the main body 3, of the rotation preventing member 8 is inserted into the rotation-prevented portion 46. Therefore, the movement of the chuck portion 4 in the peripheral direction is restricted.

The inner sealing portion 5 is deformed to tighten and hold the inserting member 2 and closely contacts, in a watertight manner, both the movement restricting portion 7 and the inserting member 2, and blocks a gap between the inserting member 2 and the movement restricting portion 7. The inner sealing portion 5 is arranged between the inner peripheral surface of the movement restricting portion 7 and the outer peripheral surface of the inserting member 2. The inner sealing portion 5 is arranged so as to surround the inserting member 2.

The inner sealing portion 5 has a through-hole 52, an abutment portion 54, and a relief portion 56.

The inserting member 2 is inserted to the through-hole 52 to allow the inner periphery of the through-hole 52 to be in close contact onto the outer periphery 22 of the inserting member 2. The inner sealing portion 5 elastically deforms so that the inner periphery of the through-hole 52 presses the outer periphery 22 of the inserting member 2. The inner sealing portion 5 in the embodiment is an annular-shaped body.

The abutment portion 54 abuts the movement restricting portion 7 or the chuck portion 4 and deforms. In the embodiment, the abutment portion 54 has a chuck portion-side abutment portion 54a and a restricting portion-side abutment portion 54b. The chuck portion-side abutment portion 54a is formed to surround an opening to open on the second opening 32 side in the axial direction in the inner sealing portion 5 and abuts the chuck portion 4 in the axial direction. The restricting portion-side abutment portion 54b is formed to surround an opening to open on the first opening 31 side in the axial direction in the inner sealing portion 5 and abuts the movement restricting portion 7 in the axial direction.

The relief portion 56 makes deforming of the inner sealing portion 5 easy when the movement restricting portion 7 or the chuck portion 4 abuts the abutment portion 54 (54a, 54b).

In the embodiment, the relief portion 56 is an annular notch formed in the chuck portion-side abutment portion 54a to abut the corner formed by the opening end surface of the chuck portion 4 on the first opening 31 side and the outer peripheral surface being continuous with the opening end surface at the end of the chuck portion 4. In this way, when the chuck portion-side abutment portion 54a abuts the corner on the first opening 31 side of the chuck portion 4, the chuck portion-side abutment portion 54a is deformed on the relief portion 56 side in correspondence with the shape of the corner to closely contact the corner of the chuck portion 4.

The movement restricting portion 7 is fixed to the main body 3 to restrict movement of the inner sealing portion 5 and the inserting member supporting portion 6.

In the embodiment, the movement restricting portion 7 is screwed into the screwed portion 312 being provided on the inner peripheral surface of the first opening 31 of the main body 3 to be connected to the main body 3, shields the first opening 31, and holds the inserting member 2.

The movement restricting portion 7 is formed in a tubular shape, and has a main body connecting portion 71, an inner sealing portion pressing portion 72, an abutment portion 73, a chuck pressing portion 75, and a connecting operation portion 77.

The main body connecting portion 71 is connected to the main body 3 at the first opening 31 side of the main body.

The main body connecting portion 71 has, on the outer peripheral surface thereof, a screwing portion (a male screw portion in the embodiment) 712 to be screwed into the screwed portion 312, and the above-mentioned screwing portion 712 is screwed into the screwed portion 312 to allow the movement restricting portion 7 to be fixed to the main body 3.

On the inner periphery of the main body connecting portion 71, a housing portion 76 to house the inner sealing portion 5 therein is provided. When the inner sealing portion 5 is pressed to be deformed, the housing portion 76 can house therein a portion in which the inner sealing portion 5 is deformed. In the embodiment, the housing portion 76 is formed along the peripheral direction on the inner peripheral surface of the main body connecting portion 71 in a concave shape.

The inner sealing portion pressing portion 72 presses the outer periphery (the restricting portion-side abutment portion 54b) of the inner sealing portion 5 inwardly and brings the inner sealing portion 5 into close contact with the inserting member 2 in a highly watertight manner.

In the embodiment, the inner sealing portion pressing portion 72 is provided on the inner periphery of the main body connecting portion 71 and configures the housing portion 76. The inner sealing portion pressing portion 72 abuts the outer periphery (the restricting portion-side abutment portion 54b) of the inner sealing portion 5 to be fitted in the housing portion 76.

The abutment portion 73 abuts an outer periphery 6a of the inserting member supporting portion 6, causing the inserting member supporting portion 6 to be attached to the movement restricting portion 7. The abutment portion 73 abutting the outer periphery 6a of the inserting member supporting portion 6 so that the inserting member supporting portion 6 is attached to the movement restricting portion 7 with the inserting member supporting portion 6 supporting the movement restricting portion 7 in an erected state.

The chuck pressing portion 75 is inserted into the communicating portion 33 to abut the chuck portion 4.

In the embodiment, the chuck pressing portion 75 is a part to abut the restricting portion abutment portion 48 of the chuck portion 4. The chuck pressing portion 75 presses the chuck portion 4 toward the second opening 32 when the chuck pressing portion 75 moves toward the chuck portion 4 at a time of screwing with the first opening 31.

The chuck pressing portion 75 is provided on the inner peripheral surface of the tip of the movement restricting portion 7 when the movement restricting portion 7 is inserted into the first opening 31.

The chuck pressing portion 75 is formed to be continuous with the chuck portion-side abutment portion 54a. While the chuck pressing portion 75 is configured with an inclined surface having an inclined angle being identical to the inclined angle of the inclined surface of the chuck portion-side abutment portion 54a, it is not limited thereto. It suffices that the chuck pressing portion 75 has a shape capable of transmitting a force in a direction to push the chuck portion 4 toward the second opening 32 from the movement restricting portion 7 by at least a part of the chuck pressing portion 75 abutting the restricting portion abutment portion 48 of the chuck portion 4.

The connection operation portion 77 is operated when the movement restricting portion 7 is fixed to the main body 3. In the embodiment, the connection operation portion 77 is a hexagonal nut-shaped screw and is provided on the outer peripheral surface of the abutment portion 73.

The connection operation portion 77 is rotationally operated around the axis when the main body connecting portion 71 is inserted into the first opening 31 of the main body. As a result, the main body connecting portion 71 of the connection operation portion 77 is rotated, the screwing portion 712 is screwed into the screwed portion 312, and the movement restricting portion 7 is moved toward the second opening 32 so that the movement restricting portion 7 is connected to the main body 3. By screwing of the above-mentioned screwing portion 712 into the screwed portion 312 of the main body 3, the movement restricting portion 7 plays a role of shielding the first opening 31, a role of pressing the chuck portion 4, the inner sealing portion 5, and the outer sealing portion 9, and a role of holding the inserting member 2 with the inserting member 2 being inserted through the insertion target.

The outer sealing portion 9 is provided in close contact with an outer periphery 7a of the movement restricting portion 7, and the main body 3.

The outer sealing portion 9 is configured with an O ring, for example, and is housed in the concave portion 37 being formed in the main body 3. The outer sealing portion 9 watertightly blocks the gap between the outer periphery 7a of the movement restricting portion 7, and the main body 3. In this way, the outer sealing portion 9 prevents liquid from flowing into the main body 3 from between the outer periphery 7a of the movement restricting portion 7 and the main body 3 toward the second opening 32 in the main body 3. In a case that the outer sealing portion 9 is an O ring, a concave portion extending in the peripheral direction can be provided on the outer periphery 7a of the movement restricting portion 7, and the outer sealing portion 9 can be disposed in the above-mentioned concave portion. In this configuration, the outer sealing portion 9 may be configured to be provided such that the outer sealing portion 9 abuts, when the movement restricting portion 7 is connected to the main body 3, the inner periphery of the main body 3 to be deformed to be in close contact with the outer periphery 7a of the movement restricting portion 7, and the main body 3.

The inserting member supporting portion 6 is a so-called kink guard and prevents bending of the inserting member 2 and torsion in the radial direction of the inserting member 2 being led out from the movement restricting portion 7 connected to the main body 3.

The inserting member supporting portion 6 is arranged so as to surround the outer periphery of the inserting member 2 being led out from the movement restricting portion 7.

The inserting member supporting portion 6 has end portions 62, 63 provided at both ends in the length direction thereof, a supporting portion 65 to abut the outer periphery 22 of the inserting member 2 to support the inserting member 2, and a sandwiched portion 67 sandwiched by the abutment portion 73 of the movement restricting portion 7 and the inserting member 2.

In the embodiment, the inserting member supporting portion 6 is configured to have the opposite ends of the supporting portion 65 having a predetermined length as the end portions 62, 63, and prevents bending of the inserting member 2 and torsion in the radial direction of the inserting member 2 by the supporting portion 65 abutting the outer periphery 22 of the inserting member 2. In the embodiment, the inserting member supporting portion 6 is configured as a substantially circular tube-shaped body in which the supporting portion 65 is arranged in the surroundings of the inserting member 2 to communicate the end portions 62, 63 opened through the inner space. In other words, while an opening of the supporting portion 65 is provided in the end portions 62, 63, respectively, it is not limited thereto, so that it can be formed in any manner as long as the supporting portion 65 abuts the outer periphery 22 of the inserting member 2 to support the inserting member 2 to prevent bending and torsion of the inserting member 2. For example, the inserting member supporting portion 6 may be formed as a frame body abutting the inserting member 2, to which is inserted, in the longitudinal direction to sandwich and hold the inserting member, or a C-shaped tubular body.

Moreover, the inserting member supporting portion 6 can be configured to provide the supporting portion 65 with a thin portion and a thick portion in the axial direction thereof. This configuration allows the end surface of the inserting member supporting portion 6 in the axial direction to move toward a space formed by the thin portion, so that the inserting member supporting portion 6 is configured to have the flexibility compared to a circular tube without the thin portion. The inserting member supporting portion 6 being provided with the thin portion and the thick portion in the axial direction thereof can suppress torsion and swinging of the inserting member 2 by having the rigidity, and, moreover, can suppress bending of the inserting member 2 near the end of the inserting member supporting portion 6 by having the flexibility. Even when a force such that bending occurs with the other end portion 62 of the inserting member supporting portion 6 as a fulcrum acts on the inserting member 2, the inserting member supporting portion 6 deflects, and therefore, bending and torsion of the inserting member 2 is suppressed. In other words, the inserting member supporting portion 6 having the rigidity and the flexibility such that the relative movement of the inserting member 2 with respect to the main body 3 is suppressed makes it possible to alleviate a load on the human body due to displacement of the inserting member 2 in the site in which the inserting member fixing device 1 is attached. Furthermore, the inserting member supporting portion 6 supporting the inserting member 2 makes it difficult for the inserting member 2 itself to move to the inner sealing portion 5 side. As long as the inserting member supporting portion has the flexibility, the thin portion is not particularly limited. The thin portion may be provided in the entire circumferential direction of the inserting member supporting portion, or may be provided in a plurality in the axial direction thereof. While the inserting member supporting portion may be configured by a plurality of members being divided in the circumferential direction, in that case the thin portion may be provided intermittently in the circumferential direction.

Furthermore, in the inserting supporting member 6, the supporting member 65 may be configured to have the main body-side end portion 63 and the other end portion 62 and the supporting member 65 may have, on the other end portion side, an inner side member in which the inner side surface of the inner side member abuts the inserting member 2 and an outer side member provided on the outer side of the inner side member. In this case, the structure may be adopted in which the inner side member and the outer side member engage by an engaging portion of the inner side member and an engaged portion of the outer side member engaging each other. For example, in the inserting member supporting portion, the inner side member may be inserted into the outer side member being a tubular-shaped member, from the other end portion 62 side of the inner side member. With respect to the fitting structure between the inner side member and the outer side member, a configuration may be used in which an engaging convex portion is provided to the inner side member to prevent falling out of the outer side member fitted thereon from the inner side member. A plurality of the engaging convex portions (for example, protruding outwardly in a radial direction) are arranged in the longitudinal direction, and a thin portion(s) are provided between the engaging convex portions. The engaging convex portion is inclined with respect to the axial direction so that the radially outward end of the engaging convex portion is positioned on the side of the main body-side end portion relative to the radially inward end of the engaging convex portion. In this case, falling out of an outer tube portion from an inner tube portion is suppressed in case that the outer tube portion is fitted onto the inner tube portion. Between the outer peripheral surface of the inner tube portion and the inner peripheral surface of the outer tube portion, there is a gap between the convex portions. Therefore, the inserting member supporting portion configured by the inner tube portion and the outer tube portion has the flexibility and even the rigidity in comparison to a circular tube without the thin portion. Moreover, the main body-side end portion of the outer tube portion abuts the main body-side end portion of the inner side member so that an excessive curvature of the inserting member supporting portion 6 is suppressed. The inserting member supporting portion 6 can alleviate a force being transmitted to the sandwiched portion 67 on the main body-side end portion 63 due to a force acting on the inserting member 2, making it difficult to move the inserting member 2 itself toward the inner sealing portion 5.

The outer diameter of the other end portion 62 is less than the outer diameter of the main body-side end portion 63 being one end portion of the opened end portions 62, 63. Moreover, the inner diameter of each of the end portions 62, 63 is substantially equal to the outer diameter of the inserting member 2.

The inserting member supporting portion 6 has the sandwiched portion 67 on the main body-side end portion 63 side, and the inserting member supporting portion 6 is fixed to the movement restricting portion 7 via the above-mentioned sandwiched portion 67.

In the embodiment, the sandwiched portion 67 is a tubular-shaped body protruding from a part surrounding the opening at one end portion (the main body-side end portion 63) and the inserting member 2 is inserted into the sandwiched portion 67. The sandwiched portion 67 is sandwiched and held by the abutment portion 73 and the inserting member 2 inserted therethrough when it is inserted to the inner side of the abutment portion 73 of the movement restricting portion 7 to be fitted therein. Thus, it is superior in maintainability in the replacement operation of the inserting member supporting portion 6 outside the insertion target. In the embodiment, the sandwiched portion 67 is provided with a claw portion to engage the abutting portion 73, strengthening coupling of both thereof.

The inserting member supporting portion 6 and the inner sealing portion 5 are provided adjacent to each other in the axial direction of the inserting member 2 with a gap G therebetween. Specifically, in the communicating portion 33, the sandwiched portion 67 of the inserting member supporting portion 6 is arranged in separation from the inner sealing portion 5, and the gap G is formed between the sandwiched portion 67 and the inner sealing portion 5.

When the inserting member supporting portion 6 swings to cause the sandwiched portion 67 or, in other words, the main body-side end portion 63 to be displaced, the above-mentioned gap G allows the displacement of the main body-side end portion 63 of the inserting member supporting portion 6 when the inserting member 2 swings. In this way, even when the main body-side end portion 63 is displaced, the main body-side end portion 63 does not contact the inner sealing portion 5.

<Assembling of Inserting Member Fixing Device 1>

The inserting member 2 is inserted into the communicating portion 33 of the main body 3. For example, the inserting member 2 extending toward outside the body from a hole provided in the skin S is inserted through the communicating portion 33 of the main body 3 by inserting it through to the first opening 31 side from the second opening 32 of the main body 3.

The chuck portion 4 is arranged on the outer periphery of the inserting member 2. Specifically, the divided bodies 4a, 4b configuring the chuck portion 4 is arranged on the outer periphery of the inserting member 2 by being configured as a tubular body while sandwiching the inserting member 2.

The chuck portion 4 is inserted into the communicating portion 33 from the first opening 31. Here, while the contact surface 442 of the chuck portion 4 being inserted into the communicating portion 33 abuts the inclined inner peripheral surface 34 of the communicating portion 33, at this time, it does not have to abut the inclined inner peripheral surface 34 of the communicating portion 33. Moreover, the chuck portion 4, in the communicating portion 33, positions the rotation-prevented portion 46 at a position to oppose the through-hole 364 of the rotation preventing member mounting portion 36 to allow the rotation-prevented portion 46 to engage the shaft 84 of the rotation preventing member 8 inserted via the through-hole 364. In other words, the shaft 84 is inserted into the rotation-prevented portion 46.

Next, the inner sealing portion 5 is fitted on the outer periphery of the inserting member 2 on the first opening 31 side with respect to the chuck portion 4. Subsequently, the movement restricting portion 7 to which the inner sealing portion 5 is fitted is fitted to the outer periphery of the inserting member 2 by being inserted into the first opening 31 from the chuck pressing portion 75 side. Then, the screwing portion 712 of the movement restricting portion 7 is screwed into the screwed portion 312 of the communicating portion 33. The screwing portion 712 being screwed into the screwed portion 312 causes the movement restricting portion 7 to be moved toward the second opening 32 of the main body 3.

Screwing the screwing portion 712 of the movement restricting portion 7 into the screwed portion 312 of the communicating portion 33 causes the chuck pressing portion 75 of the movement restricting portion 7 to be moved in the direction of the second opening 32 and the chuck pressing portion 75 to press the restricting portion abutment portion 48 of the chuck portion 4. The chuck-side abutment portion 54a of the inner sealing portion 5 presses the sealing abutment portion 45 of the chuck portion 4.

The chuck portion 4 contacts the main body 3 at the contact surface 442 by pressing of the movement restricting portion 7 toward the second opening 32 so that the chuck portion 4 moves inwardly in the radial direction of the inserting member 2 by a reaction force receiving from the main body 3 being in contact with the chuck portion 4. In other words, in proceeding with screwing of the screwing portion 712 into the screwed portion 312, the contact between the contact surface 442 and the inclined inner peripheral surface 34 causes the movement of the chuck portion 4 to be restricted. In this way, each of the divided bodies 4a, 4b of the chuck portion 4 moves toward the central axis in the radial direction, or, in other words, are reduced in diameter, causing an occurrence of a force to hold the inserting member 2 in close contact with the main body 3. This makes it possible to assemble the inserting member fixing device 1 comprising a holding structure having a high close contactability.

When the screwing portion 712 of the movement restricting portion 7 is screwed into the screwed portion 312 of the communicating portion 33 to cause the movement restricting portion 7 to be moved toward the second opening 32, or, in other words, the movement restricting portion 7 is rotated to cause the movement restricting portion 7 to be moved toward the second opening 32, a force to rotate is also transmitted to the chuck portion 4 via the chuck pressing portion 75.

However, the chuck portion 4 has the movement in the peripheral direction thereof suppressed by the rotation preventing member 8. In this way, by screwing the screwing portion 712 into the screwed portion 312, the chuck portion 4 is reduced in diameter without it co-rotating even when a force around the axis is transmitted from the movement restricting portion 7. Thus, when the screwing portion 712 of the movement restricting portion 7 is screwed into the screwed portion 312, the chuck portion 4, and the inserting member 2 being grasped by the chuck portion 4 do not co-rotate and the inserting member 2 does not twisted. The above-described assembling procedure explained above is one example, so that the assembling procedure up to screwing the screwing portion 712 of the movement restricting portion 7 into the screwed portion 312 is not particularly limited.

<Function and Effect of Inserting Member Fixing Device 1>

In the embodiment, screwing the screwing portion 712 of the movement restricting portion 7 into the screwed portion 312 of the communicating portion 33 causes the chuck pressing portion 75 of the movement restricting portion 7 to be moved toward the second opening 32. The sealing abutment portion 45 of the chuck portion 4 abuts the chuck pressing portion 75, so that the movement restricting portion 7 presses the chuck portion 4 in the axial direction of the communicating portion 33. Here, an inclined surface of the sealing abutment portion 45 of the chuck portion 4 and of the chuck pressing portion 75 of the movement restricting portion 7 are in a surface contact with each other, so that a force causing the chuck pressing portion 75 to be moved toward the second opening 32 by screwing of the screwing portion 712 into the screwed portion 312 is efficiently transmitted to the chuck portion 4.

The force transmitted to the chuck portion 4 reduces the chuck portion 4 in diameter, making it possible to firmly bring the chuck portion 4 into close contact, in a watertight manner, with the inserting member 2. Moreover, the chuck portion 4 and the inner sealing portion 5 can also be fixed by bringing them into close contact with each other in a watertight manner. Furthermore, the watertightness between the communicating portion 33 and the movement restricting portion 7 can also be secured to tightly seal the first opening 31.

Moreover, according to the inserting member fixing device of the embodiment, in the communicating portion 33, the sandwiched portion 67 of the inserting member supporting portion 6 is arranged in separation from the inner sealing portion 5, and the gap G is formed between the sandwiched portion 67 and the inner sealing portion 5.

In this configuration, in a case that the inserting member 2 makes a large swing in the torsion direction or the bending direction, a force can be transmitted to the inserting member supporting portion 6 which the outer periphery of the inserting member 2 abuts, and the inserting member supporting portion 6 may be displaced such that the inserting member 2 makes a large swing with respect to the axis of the inserting member 2. In this case, a force applied to the inserting member supporting portion 6 also causes the inserting member supporting portion 6 to follow the inserting member 2 to be displaced to be moved toward the inner sealing portion 5 being adjacent to the sandwiched portion 67 on the main body-side end portion 63 side. In this way, even when the inserting member supporting portion 6 (specifically, the sandwiched portion 67) is moved toward the inner sealing portion 5, the displacement of the inserting member supporting portion 6 as mentioned above can be absorbed with the gap G, making it possible to prevent the effect on the inner sealing portion 5. In other words, even an occurrence of a swing of the inserting member supporting portion 6 does not affect at all the close contact state of the inner sealing portion 5 being in close contact with the inserting member 2, making it possible to secure a sealing (the tightly sealed state) between the inserting member 2 and the movement restricting portion 7 by the inner sealing portion 5.

Thus, according to the invention, suppressing of swinging of an inserting member such as a driveline and securing of a sealing can be made compatible.

In the above, an embodiment of the invention has been explained. The above explanations illustrate a preferred embodiment of the invention, so that the scope of the invention is not limited thereto. In other words, explanations on the configuration of the above-described device or the shape of each of the portions represent one set of examples so that it is clearly that various changes and additions can be made to these examples within the scope of the invention.

The entire contents of the specification, the drawings, and the abstract included in the Japanese Application of the Japanese Patent Application No. 2018-222563 filed on Nov. 28, 2018 are hereby incorporated by reference.

INDUSTRIAL APPLICABILITY

The inserting member fixing device according to the invention has the effect that suppressing of swinging of an inserting member such as a driveline and securing of a sealing can be made compatible, and is useful for use in a fixing device of a medical tube being mounted onto the surface of the body and disposed continuously across the interior and the exterior of the body, for example.

DESCRIPTION OF REFERENCE NUMERALS

1 INSERTING MEMBER FIXING DEVICE
2 INSERTING MEMBER

3 MAIN BODY
4 CHUCK PORTION
4a, 4b DIVIDED BODY
5 INNER SEALING PORTION
6 INSERTING MEMBER SUPPORTING PORTION
6a, 7a OUTER PERIPHERY
7 MOVEMENT RESTRICTING PORTION
8 ROTATION PREVENTING MEMBER
82 HEAD
84 SHAFT
9 OUTER SEALING PORTION
22 OUTER PERIPHERY
31 FIRST OPENING
32 SECOND OPENING
33 COMMUNICATING PORTION
34 INCLINED INNER PERIPHERAL SURFACE
35 FIXING PORTION
36 ROTATION PREVENTING MEMBER MOUNTING PORTION
37 CONCAVE PORTION
42 INSERTION PORTION
44 CONTACT PORTION
45 SEALING ABUTMENT PORTION
46 ROTATION-PREVENTED PORTION
48 RESTRICTING PORTION ABUTMENT PORTION
52 THROUGH-HOLE
54 ABUTMENT PORTION
54a CHUCK PORTION-SIDE ABUTMENT PORTION
54b RESTRICTING PORTION-SIDE ABUTMENT PORTION
56 RELIEF PORTION
62 THE OTHER END PORTION
63 MAIN BODY-SIDE END PORTION
65 SUPPORTING PORTION
67 SANDWICHED PORTION
71 MAIN BODY CONNECTING PORTION
72 INNER SEALING PORTION PRESSING PORTION
73 ABUTMENT PORTION
75 CHUCK PRESSING PORTION
76 HOUSING PORTION
77 CONNECTION OPERATION PORTION
86 SEALING PORTION
S1 HOLE
312 SCREWED PORTION
352 FLANGE PORTION
362 BASE PORTION
364 THROUGH-HOLE
442 CONTACT SURFACE
712 SCREWING PORTION

The invention claimed is:

1. An inserting member fixing device to fix a linear inserting member to an insertion target, the inserting member fixing device comprising:
a main body;
a chuck portion to grasp the inserting member;
an inner sealing portion to be brought into close contact with an outer periphery of the inserting member;
an inserting member supporting portion to support the inserting member to maintain the inserting member being in a line shape; and
a movement restricting portion to restrict movement of the inner sealing portion and the inserting member supporting portion, wherein
the main body has a first opening, a second opening, and a communicating portion to communicate the first opening and the second opening, and a fixing portion to be fixed to the insertion target,
the chuck portion has an insertion portion to which the inserting member is inserted, and a contact portion being provided on an outer periphery of the chuck portion to contact an inner wall of the communicating portion of the main body;
the inner sealing portion has a through-hole to which the inserting member is inserted to allow an inner periphery of the through-hole to be in close contact onto the outer periphery of the inserting member,
the movement restricting portion has a main body connecting portion to be connected to the main body at the first opening side of the main body, an inner sealing portion pressing portion to press an outer periphery of the inner sealing portion inwardly, and an abutment portion to abut an outer periphery of the inserting member supporting portion,
the inserting member supporting portion has end portions provided at both ends in a length direction, a supporting portion to abut the outer periphery of the inserting member to support the inserting member, and a sandwiched portion sandwiched and held by the abutment portion of the movement restricting portion and the inserting member,
the inserting member supporting portion and the inner sealing portion are provided adjacent to each other in an axial direction of the inserting member, and
a space is provided between the inserting member supporting portion and the inner sealing portion so that a main body-side end portion of the inserting member supporting portion is displaceable when the inserting member swings.

2. The inserting member fixing device according to claim 1, comprising an outer sealing portion in close contact with an outer periphery of the movement restricting portion and the main body to prevent liquid from flowing to inside of the main body from between the outer periphery of the movement restricting portion and the main body.

3. The inserting member fixing device according to claim 1, wherein the inner sealing portion has
an abutment portion to abut the movement restricting portion or the chuck portion and to be deformed, and
a relief portion to make deforming of the inner sealing portion easy when the movement restricting portion or the chuck portion abuts the abutment portion.

4. The inserting member fixing device according to claim 1, wherein a screwed portion screwed with the main body connecting portion of the movement restricting portion is provided at an opening side of the first opening,
the movement restricting portion has a chuck pressing portion to press the chuck portion toward the second opening when the movement restricting portion moves toward the chuck portion at a time of screwing with the first opening, and
the chuck portion has a contact surface to contact the main body by pressing of the movement restricting portion toward the second opening so that the chuck portion moves inwardly in a radial direction of the inserting member by a reaction force received from the main body being in contact with the chuck portion.

* * * * *